United States Patent [19]
Ludwig et al.

[11] Patent Number: 5,311,129
[45] Date of Patent: May 10, 1994

[54] LOCAL MAGNETIC FIELD MEASUREMENT APPARATUS HAVING GRADIOMETERS ARRANGED ON NON-PARALLEL, NON-ORTHOGONAL SURFACES

[75] Inventors: Wolfgang Ludwig, Tägerwilen; Wolfgang Eschner, Friedrichshafen, both of Fed. Rep. of Germany

[73] Assignee: Dornier GmbH, Fed. Rep. of Germany

[21] Appl. No.: 923,422

[22] Filed: Aug. 3, 1992

Related U.S. Application Data

[63] Continuation-in-part of Ser. No. 656,416, Feb. 15, 1991.

[30] Foreign Application Priority Data

Feb. 2, 1990 [DE] Fed. Rep. of Germany ....... 4003115
Jan. 31, 1991 [DE] Fed. Rep. of Germany ....... 4125733

[51] Int. Cl.$^5$ ................. G01R 33/022; G01R 33/035
[52] U.S. Cl. .................................... 324/247; 324/248; 505/846
[58] Field of Search ............... 324/247, 248, 249, 260, 324/345; 128/653.1; 505/846

[56] References Cited

U.S. PATENT DOCUMENTS 4,646,025  2/1987  Martin et al. .................. 324/248 X

FOREIGN PATENT DOCUMENTS 4005079  2/1990  Fed. Rep. of Germany .
131083  6/1988  Japan ................................. 324/248

OTHER PUBLICATIONS

Wikswo, John P.; Optimization of SQUID Differential Magnetometers AIP Conference Proceedings, No. 44, pp. 145–149 (1978) (no month).
Wynn et al; "Advanced Superconducting Gradiometer/Magnetometer Arrays . . . and Technique", IEEE Trans. on Magnetics, vol. MAG-11, No. 2, Mar. 1975, pp. 701–707.

*Primary Examiner*—Gerard R. Strecker
*Attorney, Agent, or Firm*—Evenson, McKeown, Edwards & Lenahan

[57] ABSTRACT

For the determination of all linearly independent components of an Nth order gradient tensor of a magnetic field, at least $3+2N$ planar gradiometers of the Nth order are arranged on at least 3 non-parallel and non-orthogonal surfaces. As a result, three-dimensional coil structures are not necessary.

20 Claims, 2 Drawing Sheets

LOCAL MAGNETIC FIELD MEASUREMENT APPARATUS HAVING GRADIOMETERS ARRANGED ON NON-PARALLEL, NON-ORTHOGONAL SURFACES

This is a continuation-in-part of application Ser. No. 07/656,416 filed Feb. 15, 1991.

BACKGROUND AND SUMMARY OF THE INVENTION

This invention relates to an arrangement for measuring all independent components of a gradient Nth order tensor of a magnetic field (where $N \geq 1$).

To characterize a local magnetic field distribution, the knowledge of the magnetic field components as well as of the spatial derivatives of a higher order is required. This is demonstrated, for example, in Taylor's series expansion of the magnetic field vector B (x):

$$B(\overline{X}) = B\big|_o + \nabla B\big|_o \overline{X} + \tfrac{1}{2}\nabla^2 B\big|_o (\overline{X})^2 + \ldots = \sum_{N=0}^{\infty} \frac{1}{N!} \nabla^N B\big|_o (\overline{X})^N$$

wherein $-\nabla^N B \big|_o-$; is the Nth order gradient tensor taken at the origin of a system of coordinates, and contains Nth order derivatives of the magnetic field components $B_x$, $B_y$, $B_z$ according to the spatial coordinates x, y, z. An Nth order gradient tensor contains $3+2N$ linearly independent components.

A measuring apparatus, by means of which the Nth order derivatives of the magnetic field can be measured, is called a gradiometer of the Nth order. In the sense of this definition, a magnetometer, for example, by means of which the magnetic field components $B_x$, $B_y$, $B_z$ are measured, is a gradiometer of the 0th order.

A gradiometer of the Nth order comprises at least $N+1$ field receiving coils, with more than $N+1$ of such coils also being required to measure certain components.

The more precisely the local field distribution is known in one location, the more precisely it can be reconstructed or extrapolated at another location. This is significant particularly for the compensation of gradiometer arrangement, as they are used in biomagnetic measuring techniques or in the detection of magnetic anomalies. By means of conventional wire-wound three-dimensional coil arrangements, it is possible to detect all components of a gradient tensor of the Nth order (particularly for $N>1$) only with high space requirements and very high mechanical expenditures. In addition, wound coils usually have relatively large errors. A gradiometer of this type is described, for example, in Wynn, et. al.: "Advanced Superconducting Gradiometer/Magnetometer Arrays and a Novel Signal Processing Technique", *IEEE Transactions on Magnetics*, Vol. Mag. - 11, No. 2, 1975, Pages 701-707.

Planar coils can be easily produced in thin-layer configurations in a manner that is known per se. However, such two-dimensional coil arrangements, as used for example in the case of SQUIDS, are not sufficient to measure all linearly independent gradient components. For example, in the case of a 1st gradient tensor, they are sufficient only to measure the non-diagonal elements. Thus, by means of two coils situated in the x-y plane, the gradients $dB_z/dx$ and $dB_z/dy$ can be determined. For the gradient $dB_z/dz$, the coils must be disposed above one another in two planes, which is difficult to achieve by means of planar elements. In thin-layer technology, it is difficult to produce three-dimensional structures; for example, to draw coatings over edges.

U.S. Pat. No. 4,646,025, discloses an arrangement in which two coils disposed one above the other in different planes are used to measure the diagonal elements, and two coils disposed in the same plane are used to measure the non-diagonal element.

The above-described problems occur also in the case of the determination of the gradient tensors with $N>1$.

It is an object of the present invention to provide an arrangement for the determination of all linearly independent components of an Nth order gradient tensor of a magnetic field, which avoids the above-mentioned disadvantages.

In the German Patent Application P 40 05 079.3-35, this object is achieved for the measurement of the components of a 1st order gradient tensor ($N=1$). According to the present invention, the object is achieved for $N \geq 1$ by the arrangement of several planar gradiometers of the Nth order, whereby the complete Nth order gradient tensor can be calculated in a single and precise manner. As a minimum, at least $3+2N$ planar gradiometers of the Nth order are required on at least 3 non-parallel and nonorthogonal surfaces. A planar gradiometer, in this case, is a gradiometer whose field receiving coils are all situated in a single plane.

On a single plane, a maximum of $N+1$ coplanar, linearly independent gradiometers can be mounted. (Linearly independent gradiometers are those which measure linearly independent components and, in the following, are also called orthogonal gradiometers. Gradiometers are said to be coplanar when all field receiving coils of all gradiometers are situated in a common plane. Preferably, on at least two surfaces, $N+1$ coplanar gradiometers of the Nth order are arranged which measure respective linearly independent components.

Advantageously, on at least one plane, in addition to the existing gradiometers of the Nth order, additional coplanar gradiometers of lower order may also be situated. In a particularly advantageous arrangement, the following gradiometers are situated on the same plane:

$N+1$ gradiometers of the Nth order

N gradiometers of the (N−1)th order

N−1 gradiometers of the (N−2)th order gradiometer of the 0th order, for a total of $((N+1)*(N+2))/2$ gradiometers, with gradiometers of the same order measuring orthogonal components.

So that the interaction of the gradiometer field receiving coils will be minimal, each of the coils advantageously comprises only a single winding. A further reduction of the interaction may be achieved by the arrangement of the field receiving coils of each individual gradiometer in the form of a matrix. In this case, the field receiving coils of a gradiometer of the Nth order must be arranged in $m+1$ rows and $n+1$ columns, with the additional requirement that $m+n=N$. The rows and columns each have a differentiating direction; for example, in the x, y or z-axis. The coil surface of the field receiving coil in row i and column j is determined by the following equation:

$$Aij = A_o * \left[ \frac{1}{2^m} \binom{m}{i} (-1)^i \right] * \left[ \frac{1}{2^N} \binom{n}{j} (-1)^j \right]$$

wherein $i=0,...,m$ and $j=0,...,n$.

In this case, the preceding sign indicates the positive or negative winding direction; $A\cdot$ indicates the overall surface of the gradiometer which may, for example, be constructed in the shape of a square. The symbol "*" is the multiplying operator.

When this equation is satisfied by each gradiometer, the mutual interactions of the gradiometers are minimized when all gradiometers situated on the same surface are centered, and are layered above one another in a flush manner.

The invention has the following advantages:

Since all gradiometers situated on the same surface can be integrated on a single chip, optimum numerical alignment is possible in order to suppress interferences.

Wound coils with their normally large errors are avoided. Complicated layering processes, in which superconducting connections must be drawn over edges, are unnecessary.

The arrangement according to the invention is particularly suitable for the following applications:

Detection of ammunition remnants, mines, etc. with the possibility of shape recognition;

Diagnostic equipment for measuring magnetocardiograms and magnetoencephalograms with or without the use of shielding chambers;

Determination of the site and orientation of a magnetic test piece in the intracorporal region, for example, in surgery/endoscopy;

Geoprospecting by means of air-supported and stationary systems;

Nondestructive testing of materials (low-frequency eddy-flow process for thick-walled components for interior testing of cracks from the outside).

Other objects, advantages and novel features of the present invention will become apparent from the following detailed description of the invention when considered in conjunction with the accompanying drawings.

DETAILED DESCRIPTION OF THE DRAWINGS

Figure 1:
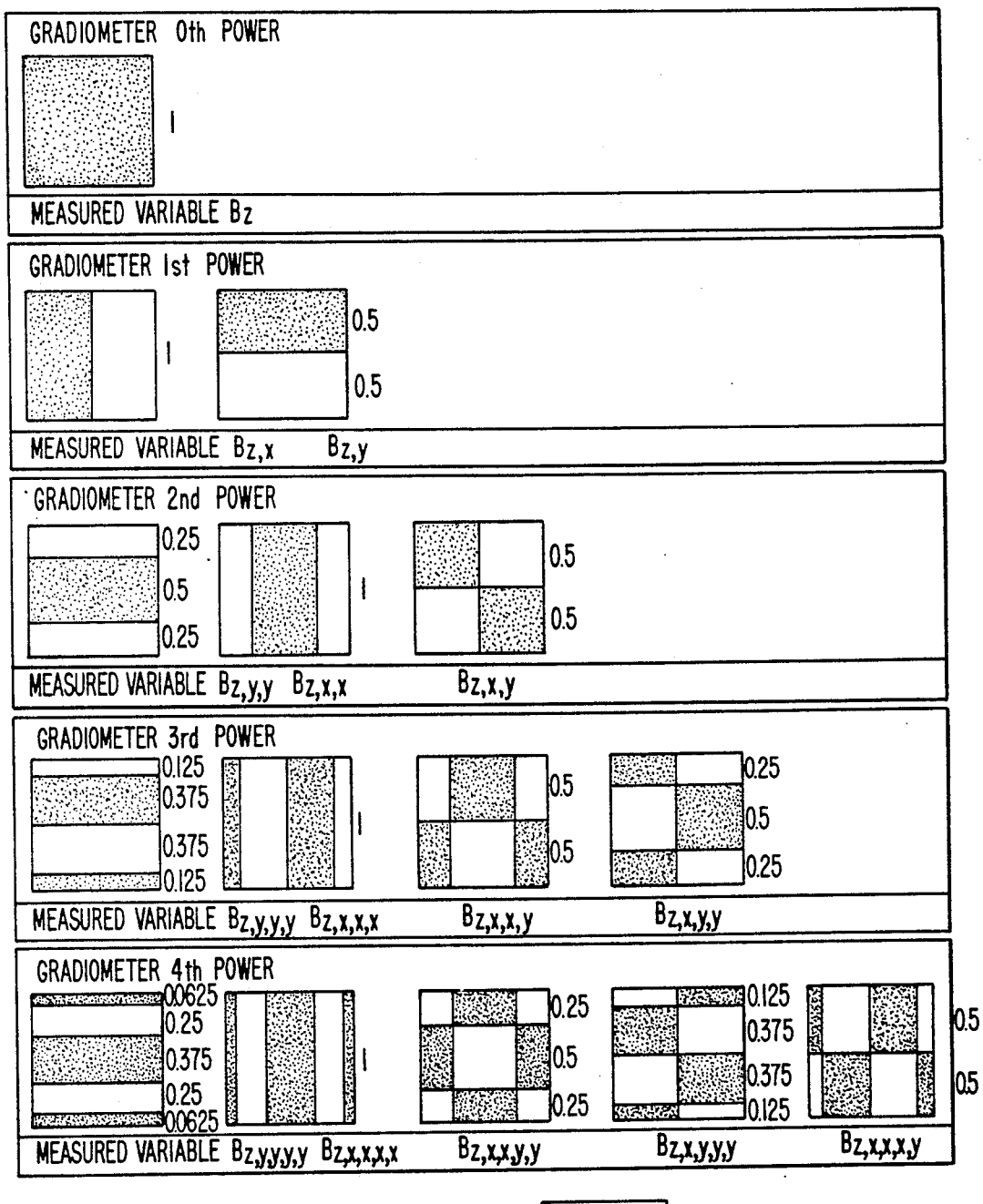
FIG. 1. is a view of planar gradiometers of the 0th to 4th order according to the invention.

FIG. 1 illustrates examples of planar gradiometers of the 0th to 4th order used in the measurement apparatus according to the invention. In each row, $N+1$ orthogonal gradiometers respectively of the Nth order are indicated. In each case it is indicated which components of the gradient tensor can be measured by means of the individual gradiometers. In this case, it is a prerequisite that the shown gradiometers are situated on the x/y-plane of a system of coordinates. The designation $B_{z,x,y}$, for example, indicates the derivative of the z-component of the magnetic field according to the spatial coordinates x and y.

The black and white areas represent the coil surfaces of the individual field receiving coils of a gradiometer. Thus, the coil windings must be considered to be the borders of the black and white surfaces. A black surface indicates a positive winding direction; a white surface indicates a negative winding direction. The individual field receiving coils need not necessarily be square or rectangular. Moreover, it is also possible that there are spaces between the coils.

All of the gradiometers illustrated in FIG. 1 satisfy the above-mentioned equation for the surfaces of the field receiving coils. The values for m and n from the above-mentioned formula, for example, for the illustrated gradiometers of the 4th order are from left to right: $(m,n)=(4,0), (0,4), (2,2), (3,1) (1,3)$. The dimension figures on the right margin indicate the width of the corresponding surfaces relative to the overall width of the gradiometer.

Figure 2:
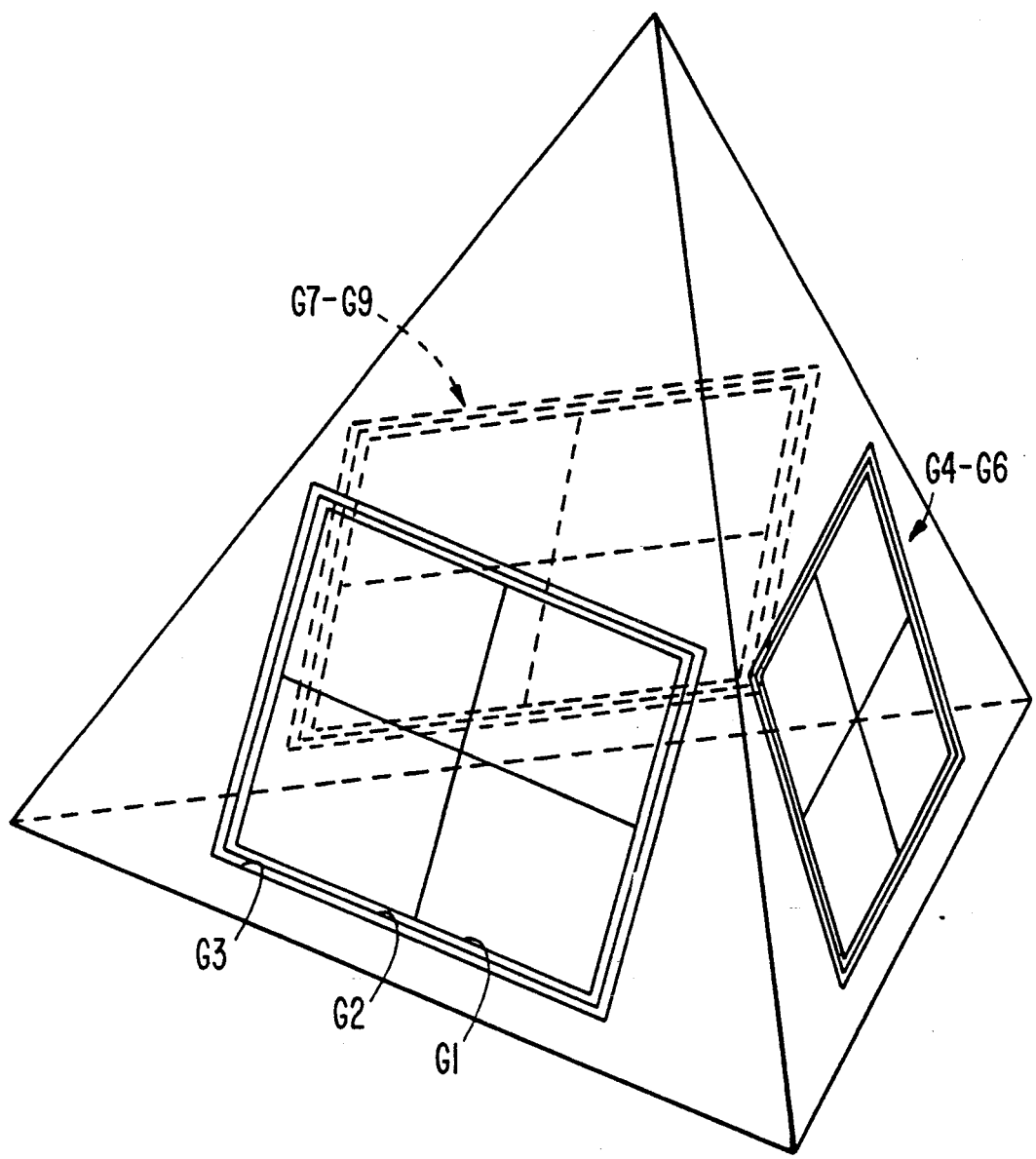
FIG. 2 is a perspective view of an arrangement of planar gradiometers according to the invention.

FIG. 2 illustrates an arrangement of planar gradiometers G1-G9 according to the invention, on three surfaces of a tetrahedron for measuring the components of a gradient tensor of the 2nd order. On each of the three surfaces of the tetrahedron, three orthogonal planar gradiometers G1-G3, G4-G6, G7-G9 respectively are arranged in layers above one another; for example, those shown in Column 3 of FIG. 1. The gradiometers are all arranged on the same surface and are layered above one another in a centered and flush manner. The gradiometers situated underneath are indicated symbolically by projecting edges.

The manufacture of such gradiometers disposed above one another is performed by well known methods of thin-layer or thin film technology, such as, for example by vacuum evaporation, in which a thin film is deposited on a substrate by evaporation from a boiling source in the presence of a hard vacuum. Other well known methods are, for example, sputtering or laser ablation. Thin insulating layers are, in each case, inserted between the gradiometers.

Although the invention has been described and illustrated in detail, it is to be clearly understood that the same is by way of illustration and example, and is not to be taken by way of limitation. The spirit and scope of the present invention are to be limited only by the terms of the appended claims.

We claim:

1. An arrangement for determining all linearly independent components of an Nth order gradient tensor of a magnetic field, with $N \geq 1$, comprising:
   at least planar gradiometers of the Nth order arranged on at least 3 non-parallel and non-orthogonal surfaces, said surfaces being arranged in close proximity to each other.

2. An arrangement according to claim 1, wherein the gradiometers are arranged on surfaces of a polyhedron with at least three non-parallel and non-orthogonal surfaces.

3. Arrangement according to, claim 2 wherein said polyhedron is one of: a pyramid with at least four lateral surfaces, an octahedron, a dodecahedron and an icosahedron.

4. An arrangement according to claim 1, wherein on each surface, $N+1$ gradiometers of the Nth order are arranged, which measure linearly independent components.

5. An arrangement according to claim 2, wherein on each surface, $N+1$ gradiometers of the Nth order are arranged, which measure linearly independent components.

6. An arrangement according to claim 1, wherein additional gradiometers of less than the Nth order are situated on at least one surface.

7. An arrangement according to claim 2, wherein additional gradiometers of less than the Nth order are situated on at least one surface.

8. An arrangement according to claim 4, wherein additional gradiometers of less than the Nth order are situated on at least one surface.

9. An arrangement according to claim 6, wherein the following gradiometers are situated on at least one surface:
N+1 gradiometers of the Nth order
N gradiometers of the (N−1)th order
N−1 gradiometers of the (N−2)th order
gradiometer of the 0th order.

10. An arrangement according to claim 1, wherein the gradiometers situated on the same surface are layered above one another in a centered and flush manner.

11. An arrangement according to claim 2, wherein the gradiometers situated on the same surface are layered above one another in a centered and flush manner.

12. An arrangement according to claim 4, wherein the gradiometers situated on the same surface are layered above one another in a centered and flush manner.

13. An arrangement according to claim 6, wherein the gradiometers situated on the same surface are layered above one another in a centered and flush manner.

14. An arrangement according to claim 1, wherein each field receiving coil of a gradiometer comprises only one winding.

15. An arrangement according to claim 2, wherein each field receiving coil of a gradiometer comprises only one winding.

16. An arrangement according to claim 4, wherein each field receiving coil of a gradiometer comprises only one winding.

17. An arrangement according to claim 6, wherein each field receiving coil of a gradiometer comprises only one winding.

18. An arrangement according to claim 1, wherein the field receiving coils of a gradiometer of the Nth order are arranged in a matrix of m+1 rows and n+1 columns with $m+n=N$, and wherein the following applies to the coil surface $A_{ij}$ of the field receiving coil in row i and column j:

$$A_{ij} = A_o * \left[ \frac{1}{2^m} \binom{m}{i}(-1)^i \right] * \left[ \frac{1}{2^N} \binom{n}{j}(-1)^j \right]$$

wherein $i=0, 1,..., m$ and $j=0,1,...,n$.

19. An arrangement according to claim 4, wherein the field receiving coils of a gradiometer of the Nth order are arranged in a matrix of m+1 rows and n+1 columns with $m+n=N$, and wherein the following applies to the coil surface $A_{ij}$ of the field receiving coil in row i and column j:

$$A_{ij} = A_o * \left[ \frac{1}{2^m} \binom{m}{i}(-1)^i \right] * \left[ \frac{1}{2^N} \binom{n}{j}(-1)^j \right]$$

20. An arrangement according to claim 9, wherein the field receiving coils of a gradiometer of the Nth order are arranged in a matrix of m+1 rows and n+1 columns with $m+n=N$, and wherein the following applies to the coil surface $A_{ij}$ of the field receiving coil in row i and column j:

$$A_{ij} = A_o * \left[ \frac{1}{2^m} \binom{m}{i}(-1)^i \right] * \left[ \frac{1}{2^N} \binom{n}{j}(-1)^j \right]$$

wherein $i=0, 1,..., m$ and $j=0,1,...,n$,
wherein $i=0, 1,..., m$ and $j=0,1,...,n$.

* * * * *